(12) United States Patent
Olah (10) Patent No.: US 12,389,169 B1
(45) Date of Patent: Aug. 12, 2025

(54) AUDIOGRAM, SYSTEM FOR AIDING HEARING, AND METHOD FOR USE OF SAME

(71) Applicant: Laslo Olah, Richardson, TX (US)

(72) Inventor: Laslo Olah, Richardson, TX (US)

( * ) Notice: Subject to any disclaimer, the term of this patent is extended or adjusted under 35 U.S.C. 154(b) by 0 days.

(21) Appl. No.: 19/191,380

(22) Filed: Apr. 28, 2025

Related U.S. Application Data

(63) Continuation-in-part of application No. 19/090,045, filed on Mar. 25, 2025, which is a continuation of application No. 18/779,796, filed on Jul. 22, 2024, now Pat. No. 12,262,179, which is a continuation-in-part of application No. 18/634,077, filed on Apr. 12, 2024, now Pat. No. 12,108,220.

(60) Provisional application No. 63/775,197, filed on Mar. 20, 2025, provisional application No. 63/632,371, filed on Apr. 10, 2024, provisional application No. 63/564,110, filed on Mar. 12, 2024.

(51) Int. Cl.
*H04R 25/00* (2006.01)

(52) U.S. Cl.
CPC .......... *H04R 25/50* (2013.01); *H04R 25/305* (2013.01); *H04R 25/558* (2013.01); *H04R 25/609* (2019.05); *H04R 25/70* (2013.01)

(58) Field of Classification Search
CPC .... H04R 25/50; H04R 25/609; H04R 25/305; H04R 25/558; H04R 25/70
USPC ....................................................... 381/314
See application file for complete search history.

(56) References Cited

FOREIGN PATENT DOCUMENTS

WO    WO-2023048499 A1 *   3/2023   ............... H04R 5/04

* cited by examiner

*Primary Examiner* — Phylesha Dabney
(74) *Attorney, Agent, or Firm* — Scott Griggs; Griggs Bergen LLP (57) ABSTRACT

A hearing aid system is disclosed that automates selection or creation of hearing profiles using a dynamically customizable vivo adaptare audiogram. The hearing aid and a smart device communicate via a programming interface, where the smart device runs processor-executable instructions for a listening intelligence and frequency enhancement function. An artificial intelligence module evaluates ambient sound, compares it to stored hearing profiles specifying frequency adjustments, and either selects one or merges multiple profiles to form a new profile. The chosen profile is activated in real time, with the option to store it for later use. Available modes include "Test and Store," capturing ambient sound to refine a profile, and real-time adaptation, which continuously applies incremental changes without repeated user input.

20 Claims, 4 Drawing Sheets

AUDIOGRAM, SYSTEM FOR AIDING HEARING, AND METHOD FOR USE OF SAME

PRIORITY STATEMENT

This application claims priority to provisional U.S. Application Ser. No. 63/775,197 entitled "Audiogram, System for Aiding Hearing, and Method for Use of Same," and filed on Mar. 20, 2025 in the name of Laslo Olah; which is hereby incorporated by reference, in entirety, for all purposes.

This application is a continuation-in-part of U.S. application Ser. No. 19/090,045 entitled, "Audiogram, System for Aiding Hearing, and Method for Use of Same" and filed on Mar. 25, 2025 in the name of Laslo Olah; which is a continuation of U.S. application Ser. No. 18/779,796 entitled "Audiogram, System for Aiding Hearing, and Method for Use of Same" and filed on Jul. 22, 2024 in the name of Laslo Olah, now U.S. Pat. No. 12,262,179 issued on Mar. 25, 2025; which is a continuation-in-part of U.S. application Ser. No. 18/634,077 entitled "System for Aiding Hearing and Method for Use of Same" and filed on Apr. 12, 2024 in the name of Laslo Olah, now U.S. Pat. No. 12,108,220 issued on Oct. 1, 2024; which claims priority from the following applications: (1) U.S. Provisional Patent Application Ser. No. 63/564,110 entitled "System for Aiding Hearing and Method for Use of Same" and filed on Mar. 12, 2024 in the name of Laslo Olah; and (2) U.S. Provisional Patent Application Ser. No. 63/632,371 entitled "System for Aiding Hearing and Method for Use of Same" and filed on Apr. 10, 2024 in the name of Laslo Olah; all of which are hereby incorporated by reference, in entirety, for all purposes.

TECHNICAL FIELD OF THE INVENTION

This invention relates, in general, to hearing tests and systems for aiding hearing and, in particular, to audiograms, systems for aiding hearing, hearing aid devices, and methods for use of the same that provide hearing testing as well as signal processing and feature sets to enhance speech and sound intelligibility.

BACKGROUND OF THE INVENTION

Traditionally, the management of hearing loss has been anchored in a process that confines the crucial step of audiogram assessment and fitting within specialized test facilities. This conventional approach necessitates that individuals seeking hearing testing, hearing improvements, or hearing aid adjustments must physically visit these facilities to undergo testing, followed by the fitting of the hearing aid according to the newly assessed audiogram. In the event of any changes in the patient's hearing capabilities or dissatisfaction with the hearing aid's performance, the cycle necessitates a return to the test facility for reassessment. This process not only imposes significant logistical challenges but also delays the optimization of hearing aid settings to accommodate evolving patient needs. Hence, there is a burgeoning need for innovative hearing aids and methodologies that transcend these traditional constraints, offering patients the flexibility to tailor their hearing experience directly, without the repeated need to revert to test facilities for adjustments.

SUMMARY OF THE INVENTION

This application presents a transformative in-situ hearing aid system that departs from static, clinic-dependent audiograms and enables real-time, user-driven customization. A vivo adaptare audiogram is embedded directly in the hearing aid device itself, allowing patients to generate, store, and refine multiple hearing profiles through a smart device application. Building on harmonics-based testing, real-life sampling (e.g., in noisy environments), and fine-grained frequency-segment manipulation, the system effectively closes down the need for repeated test-facility visits.

Central to this innovation is the listening intelligence and frequency enhancement (LIVE) function. When activated, the hearing aid device—via its microphones—captures ambient sound and transmits it to the smart device's artificial intelligence module. This module analyses the input data and compares it with a library of stored hearing profiles and either selects one or synthesizes a new profile by combining multiple profiles. The updated profile is then instantly uploaded to the hearing aid for immediate use. Users may invoke a "Test and Store" mode, which stores the newly formed profile for later recall, or select real-time adaptive mode, allowing the AI to continuously refine frequency segments without further input.

Unlike conventional systems limited to fixed, clinic-derived audiograms, the vivo adaptare approach dynamically modifies the entire audiogram itself. By slicing the hearing range into distinct segments and enabling independent adjustments (such as noise cancellation, high-frequency boosts, or harmonic calibrations), the system grants a high level of control over each band. Profiles can be layered, stored, recalled, and merged, ensuring that users can address various acoustic scenarios—restaurant noise, wind, or specialized speech enhancement—simply by selecting or generating the relevant profile.

As a result, patients can fine-tune their hearing experience at will, supported by an AI-driven architecture that continuously adapts and learns from real-world conditions. Whether mitigating excessive high-frequency noise in a restaurant, automatically switching to a wind-noise reduction profile outdoors, or combining existing profiles for a brand-new environment, the system fosters an unprecedented level of personalization and convenience. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Figure 1:
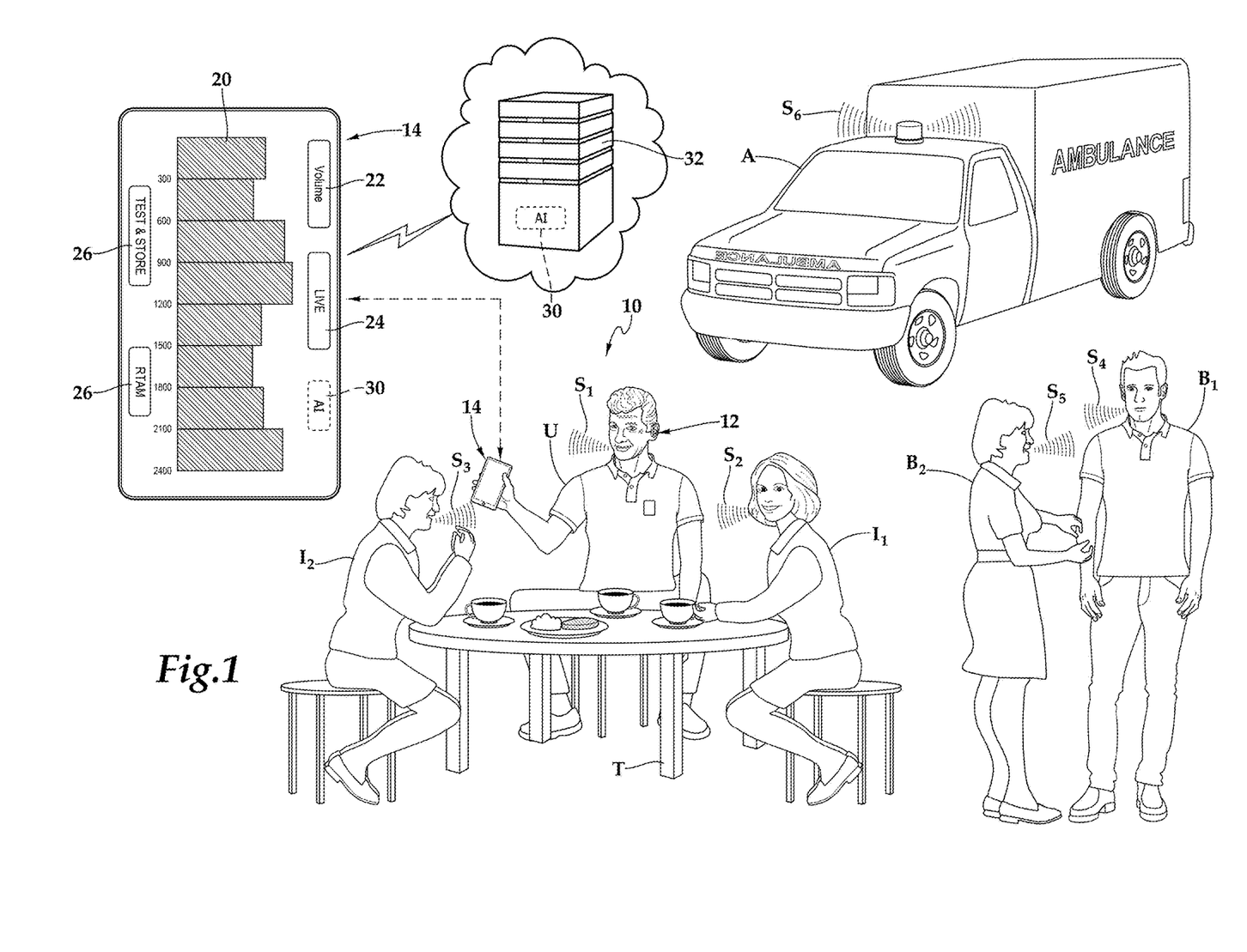
FIG. 1 is a front perspective schematic diagram depicting one embodiment of a hearing aid device being utilized according to the teachings presented herein.

Referring now to FIG. 1, an exemplary environment for a hearing aid system 10 is illustrated. A user U, who may be a patient with hearing impairment, is seated at a table T—such as in a restaurant or café—and wears a hearing aid device 12. The hearing aid device 12 includes integrated sound processing capabilities, such as a microphone for capturing ambient sound, a speaker for delivering processed audio to the user, and an electronic signal processor capable of applying stored hearing profiles. In this setting, multiple background sounds are present: for instance, individuals I1 and I2 generate sounds S2 and S3, while bystanders B1 and B2 produce sounds S4 and S5. An ambulance A, passing by, emits a dominant sound S6.

In the illustrated embodiment, the hearing aid device 12 communicates bidirectionally with a smart device 14, which may be a smartphone, smartwatch, tablet, or wearable. The smart device 14 includes a processor, a transceiver, a user interface, non-transitory memory, and storage. Through this user interface, a listening intelligence and frequency enhancement (LIVE) function may be presented, allowing the patient to initiate an automated analysis of the ambient sound environment. Upon activation, sound data captured by the hearing aid device 12's microphone is transmitted to the smart device 14, where an artificial intelligence module compares it to a plurality of stored hearing profiles in a vivo adaptare audiogram 20. Depending on the user's selection or the AI's recommendation, the hearing aid device 12 can operate in a test and store mode—capturing ambient sound for a set duration and creating or modifying a hearing profile—or in real-time adaptive mode (RTAM), where incremental adjustments to specific frequency segments are continuously uploaded to the hearing aid device 12 without requiring repeated user confirmations. To implement these various functionalities, various user interfaces are provided on the smart device, including, for example, volume 22, LIVE 24, Test and Store 26, and RTAM 28. Further, as shown AI 30 may be embodied on the smart phone 14 or a server 32, or both. Accordingly, FIG. 1 depicts both the physical arrangement of user U, hearing aid device 12, and their acoustic environment, as well as the conceptual link to smart device 14, thereby supporting the system's capability to store, select, or combine hearing profiles in real time for immediate application and future reference.

Figure 2:
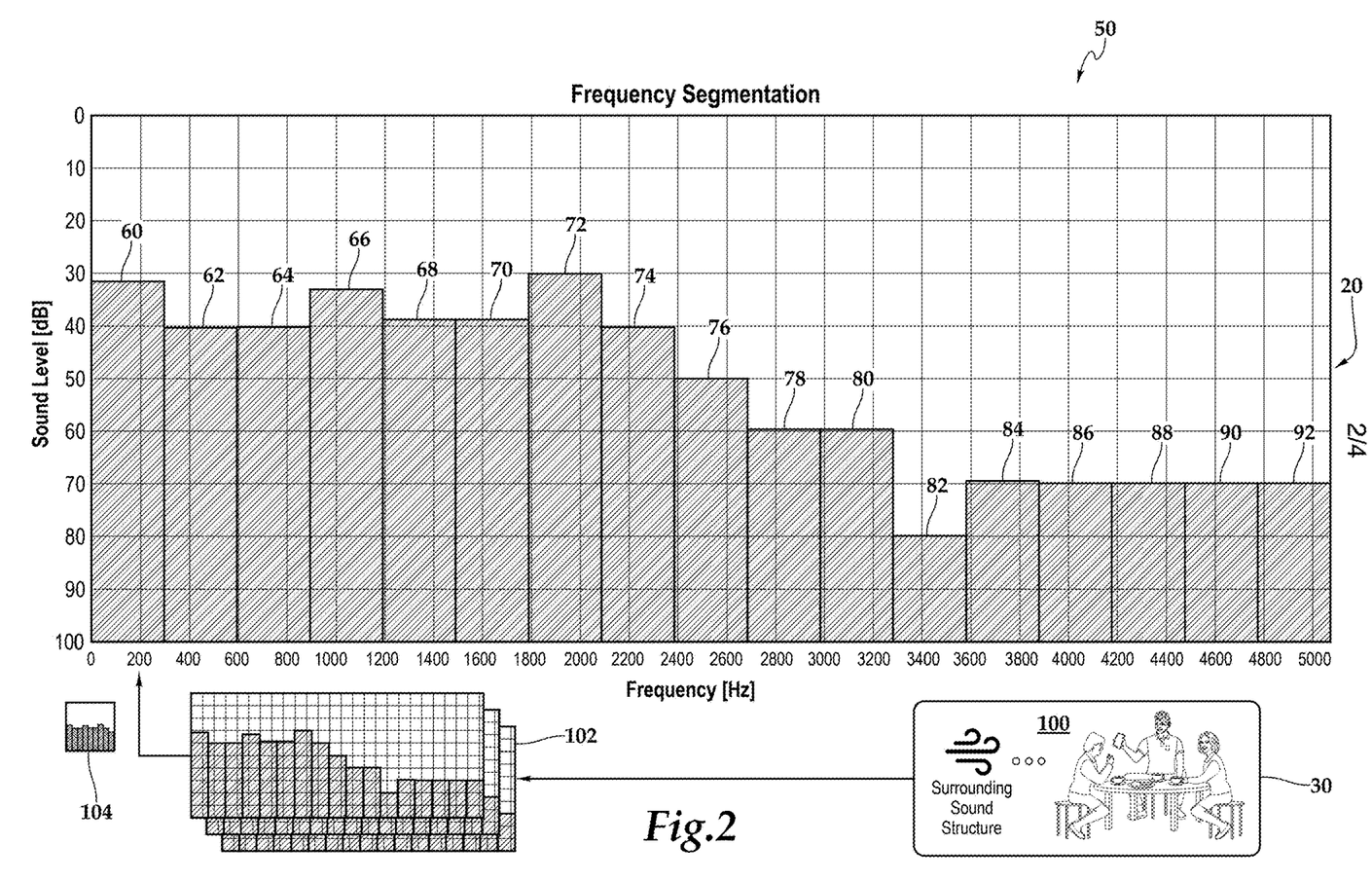
FIG. 2 is graphical representations of audiogram processing according to the teachings presented herein.

Referring now to FIG. 2, a consolidated illustration 50 depicts how a vivo adaptare audiogram evolves through various steps of testing and customization. The vivo adaptare audiogram 20 represents the user's starting hearing profile, possibly determined by a harmonics-based test, which may be segmented into discrete frequency bands 60, 62, 64, 66, 68, 70, 72, 74, 76, 78, 80, 82, 84, 86, 88, 90, 92 (e.g., low-, mid-, and high-frequency ranges), each capable of being adjusted independently. This vivo adaptare audiogram 20 reflects changes made via the listening intelligence and frequency enhancement functionality on the smart device 14. By activating the listening intelligence and frequency enhancement function, the hearing aid's microphones capture a surrounding noise structure 100—whether in a quiet home, a bustling restaurant, or an outdoor setting with wind—and transfer that data to the AI module 30. The AI module 30 either selects an existing stored profile or combines multiple profiles at library 102 to form a new set of frequency adjustments 104 that address real-time needs, such as attenuating background noise or boosting speech clarity.

Once the updated audiogram is generated, the hearing aid can operate in a test and store mode—temporarily evaluating ambient sound and saving the resultant adjustments—or in a real-time adaptive mode, continuously refining the hearing profile without user intervention. This process allows nearly unlimited storage of hearing profiles, each reflecting different acoustic conditions or personal preferences. Users may also slice the overall frequency range into additional segments or merge stored profiles to target specific hearing goals. Accordingly, FIG. 2 conveys the transformation from a baseline hearing profile to a fully customizable vivo adaptare audiogram, reinforcing the system's ability to generate, store, and apply multiple test criteria in response to dynamic environments.

Figure 3:
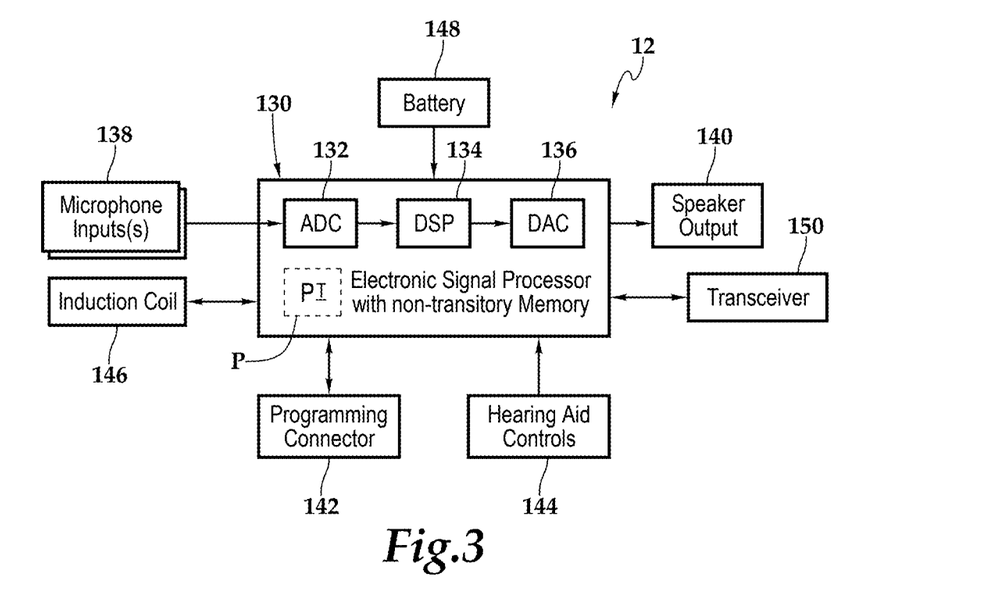
FIG. 3 is a functional block diagram depicting one embodiment of the hearing aid device shown herein.

Referring now to FIG. 3, an illustrative embodiment of the hearing aid device 12 is depicted. In one embodiment, an electronic signal processor 130 may be housed in the hearing aid device 12. The hearing aid 10 may include an electronic signal processor 130 for each ear or the electronic signal processor 130 for each ear may be at least partially integrated or fully integrated. In order to measure, filter, compress, and generate, for example, continuous real-world analog signals in form of sounds, the electronic signal processor 130 may include an analog-to-digital converter (ADC) 132, a digital signal processor (DSP) 134, and a digital-to-analog converter (DAC) 136. In some embodiments, the electronic signal processor 130, including the digital signal processor embodiment, has memory accessible to a processor as well as an interface to a programming interface P. One or more microphone inputs 138 corresponding to one or more respective microphones, a speaker output 140, various controls, such hearing aid controls 144, an induction coil 146, a battery 148, and a transceiver 150 are also housed within the hearing aid 10. An optional programming connector 142 serves as an interface between a hearing aid and a programming device, such as a computer or a dedicated hearing aid programming unit.

As shown, a signaling architecture communicatively interconnects the microphone inputs 138 to the electronic signal processor 130 and the electronic signal processor 130 to the speaker output 140. The various hearing aid controls 144, the induction coil 146, the battery 148, and the transceiver 150 are also communicatively interconnected to the electronic signal processor 130 by the signaling architecture. The speaker output 140 sends the sound output to a speaker or speakers to project sound and in particular, acoustic signals in the audio frequency band as processed by the hearing aid 10. The hearing aid controls 144 may include an ON/OFF switch as well as volume controls, for example. It should be appreciated, however, that in some embodiments, all control is manifested through the adjustment of the vivo adaptare audiogram. The induction coil 146 may receive magnetic field signals in the audio frequency band from a telephone receiver or a transmitting induction loop, for example, to provide a telecoil functionality. The induction coil 146 may also be utilized to receive remote control signals encoded on a transmitted or radiated electromagnetic carrier, with a frequency above the audio band. Various programming signals from a transmitter may also be received via the induction coil 146 or via the transceiver 150, as will be discussed. The battery 148 provides power to the hearing aid 10 and may be rechargeable or accessed through a battery compartment door (not shown), for example. The transceiver 150 may be internal, external, or a combination thereof to the housing. Further, the transceiver 150 may be a transmitter/receiver, receiver, or an antenna, for example. Communication between various smart devices and the hearing aid 10 may be enabled by a variety of wireless methodologies employed by the transceiver 150, including 802.11, 3G, 4G, Edge, WiFi, ZigBee, near field communications (NFC), Bluetooth low energy, and Bluetooth, for example.

The various controls and inputs and outputs presented above are exemplary and it should be appreciated that other types of controls may be incorporated in the hearing aid device 10. Moreover, the electronics and form of the hearing aid device 10 may vary. The hearing aid device 10 and associated electronics may include any type of headphone configuration, a behind-the-ear configuration, an in-the-ear configuration, or in-the-ear configuration, for example.

Referencing FIG. 3, the electronic signal processor 130 within the hearing aid is engineered to work with a dynamically customizable audiogram, allowing for personalization in hearing aid technology. This innovative approach permits the user U to adjust the audiogram in real-time via the smart device 14 to suit his or her unique hearing preferences and the specific demands of their auditory environment. The electronic signal processor 130, which is associated with the programming interface P, within the hearing aid device 12 allows for a range of adjustments to suit the user's individual hearing preferences and environmental needs.

In some embodiments of the system 10, the programming interface P establishes a dynamic and bidirectional communication channel between the hearing aid device 12 and the smart device 14. The programming interface P supports the direct adjustment and real-time customization of the hearing aid's settings via an application on the smart device 14. This interface enables users to actively manage and fine-tune their hearing experience by modifying the audiogram stored on the hearing aid device 12 through the smart device 14. The programming interface P ensures that any changes made to the audiogram are instantly communicated to the hearing aid, allowing for immediate application of the updated settings. This extensible architecture of the programming interface P also supports the integration of additional operational modes and functionalities, allowing for continuous improvement and expansion of the system's capabilities in response to evolving user needs and technological advances.

In doing so, in some embodiments, it enables the essential operations claimed in the system: (1) capturing ambient sound data, (2) transmitting it to an artificial intelligence module on the smart device, (3) receiving newly generated or combined hearing profiles, and (4) immediately applying these profiles for real-time processing of incoming audio signals. Through this interface, the user can invoke the LIVE function—whether in a Test and Store mode (capturing and storing a newly formed profile) or in real-time adaptive mode (continuously refining frequency segments as environmental conditions change). During operation, the signal processor 130 converts microphone-captured analog audio into digital signals, executes the user's selected hearing profile from the vivo adaptare audiogram (or a newly generated one), and outputs optimized audio to the speaker. This can include frequency-segment adjustments (e.g., boosting certain bands, attenuating background noise, or neutralizing wind noise) and advanced features such as directional sound focus. Notably, the user may store or retrieve multiple hearing profiles—some derived from harmonic tests, others from a "life sample" test in real-world conditions—thereby building a near-limitless repository of configurations.

Upon execution of the embedded instructions, the hearing aid can rank or merge existing profiles based on AI-driven criteria such as user feedback, signal-to-noise ratios, or usage history. The resulting system "closes down" the need for repeated lab-based testing by allowing the user (or the AI algorithm) to tailor the audiogram in situ at any time. This synergistic design—integrating the signal processor 130, the programming interface P, and the smart device's AI module—realizes the invention's objectives of enabling an adaptive, patient-centered hearing solution with on-demand test, store, and real-time modification capabilities.

Through the programming interface P, the user interface on the smart device 14 can present intuitive controls for the LIVE function. The system may further support specialized operational modes (e.g., "Test and Store" vs. "Real-Time Adaptation") and additional features such as volume control, impulse noise reduction, and wind noise reduction. This extensible architecture ensures that future updates—whether through firmware or software—can integrate seamlessly, continuously improving the hearing experience in response to user needs and emerging technologies.

Figure 4:
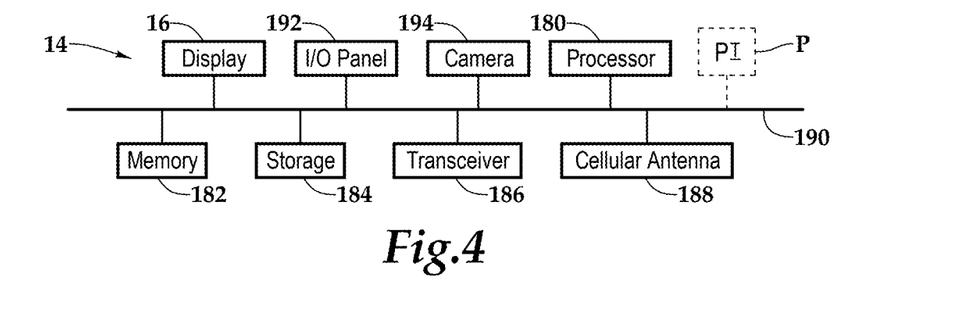
FIG. 4 is a functional block diagram depicting one embodiment of a smart device shown in FIG. 1, which may form a pairing with the hearing aid.

Referring now to FIG. 4, the proximate smart device 14 may be a wireless communication device of the type including various fixed, mobile, and/or portable devices. To expand rather than limit the discussion of the proximate smart device 14, such devices may include, but are not limited to, cellular or mobile smart phones, tablet computers, smartwatches, wearables, and so forth. The proximate smart device 14 may include a processor 180, memory 182, storage 184, a transceiver 186, and a cellular antenna 188 interconnected by a busing architecture 190 that also supports the display 16, I/O panel 192, and a camera 194. The programming interface P is associated with the processor 180 and possibly other components of the busing architecture 190. It should be appreciated that although a particular architecture is explained, other designs and layouts are within the teachings presented herein.

In operation, the programming interface P establishes a bidirectional link between the hearing aid device 12 and the smart device 14. Pursuant to the claims, the non-transitory memory 182 stores processor-executable instructions that, when executed by processor 180, enable the LIVE function's core operations. Specifically, these instructions allow the smart device 14 to:

Present a user interface showcasing the LIVE function, including "Test and Store" or real-time adaptive modes, Receive ambient sound data captured by the hearing aid's microphones, Utilize an artificial intelligence module to compare the incoming data against one or more stored hearing profiles, and Transmit updated or newly generated hearing profiles back to the hearing aid device 12 for immediate application.

This architecture supports the invention's objective of accommodating virtually unlimited test criteria—ranging from harmonics-based hearing tests to user-generated "life samples" recorded in noisy settings. The user can rapidly form new profiles by segmenting the frequency range and setting desired amplification or attenuation levels. These tailored profiles may be stored within the hearing aid's vivo adaptare audiogram for future recall or seamlessly merged to address changing environments.

In certain embodiments, the artificial-intelligence functions, signal-processing workload, and even the vivo adaptare audiogram itself are partitioned across the hearing-aid device 12, the smart device 14, and/or a remote or cloud-based server 32. Latency-critical operations—such as real-time filtering, amplification, and output shaping—remain on the electronic signal processor 130 inside the hearing aid, while mid-tier analytics and user-interface logic can execute on the processor 180 of the smart device. Computationally intensive tasks (e.g., large-scale pattern recognition, profile ranking, or synthesis of composite profiles) may be off-loaded to one or more servers that synchronize with the smart device when connectivity allows. Likewise, the vivo adaptare audiogram may be mirrored or sharded among these components so that the most current profile data is always accessible to whichever element is best positioned to act. This modular, distributed architecture lets the system dynamically allocate resources based on processing power, battery life, network availability, and user privacy preferences, thereby further eliminating reliance on repeated clinic-based audiogram updates and enabling in-the-field creation, refinement, and deployment of hearing profiles.

To accommodate scenarios in which the smart device 14 is unavailable—such as when a patient programs the hearing aid device 12 at home and subsequently leaves the smart device 14 behind—the system 10 provides an autonomous "detached-operation" mode resident entirely within the hearing aid. Before separation, the smart device synchronizes the most recent vivo adaptare audiogram (including all stored and composite profiles) and transfers a lightweight inference model to the electronic signal processor 130. While detached, in some embodiments, the hearing aid device 12 (i) listens for acoustic triggers that map to pre-stored profiles (e.g., broadband crowd noise above a configurable threshold, impulsive clatter characteristic of dishware, sustained low-frequency wind), (ii) autonomously selects or blends the corresponding profiles, and (iii) applies the resulting frequency-segment adjustments in real time without external guidance. All profile selections, ambient-sound descriptors, and user-initiated control inputs (such as on-device volume taps) are logged locally in non-volatile memory. When the smart device 14 or a server 32 connection is re-established, the hearing aid uploads the log, allowing the AI module to refine ranking weights, generate improved composite profiles, and push any firmware or audiogram updates back to the device. In this way, the system preserves full hearing-enhancement functionality—and a learning feedback loop—even when the patient elects to operate the hearing aid wholly independently of the smart device.

Beyond simply pairing with the hearing aid device 12, the processor 180 in the smart device 14 can further generate status reports, track profile usage statistics, or facilitate user feedback for fine-tuning the AI's recommendations (e.g., rating comfort or clarity in certain noise environments). This level of interoperability empowers the patient to store, retrieve, or combine hearing profiles at will, ensuring a truly user-centric approach to hearing enhancement—whether switching to a restaurant-optimized profile, a wind-noise-attenuating profile, or testing new frequency-segment adjustments on-the-fly. By unifying the user interface, AI processing, and memory resources under one system, the invention delivers a robust platform for personalized, real-time hearing assistance.

Figure 5:
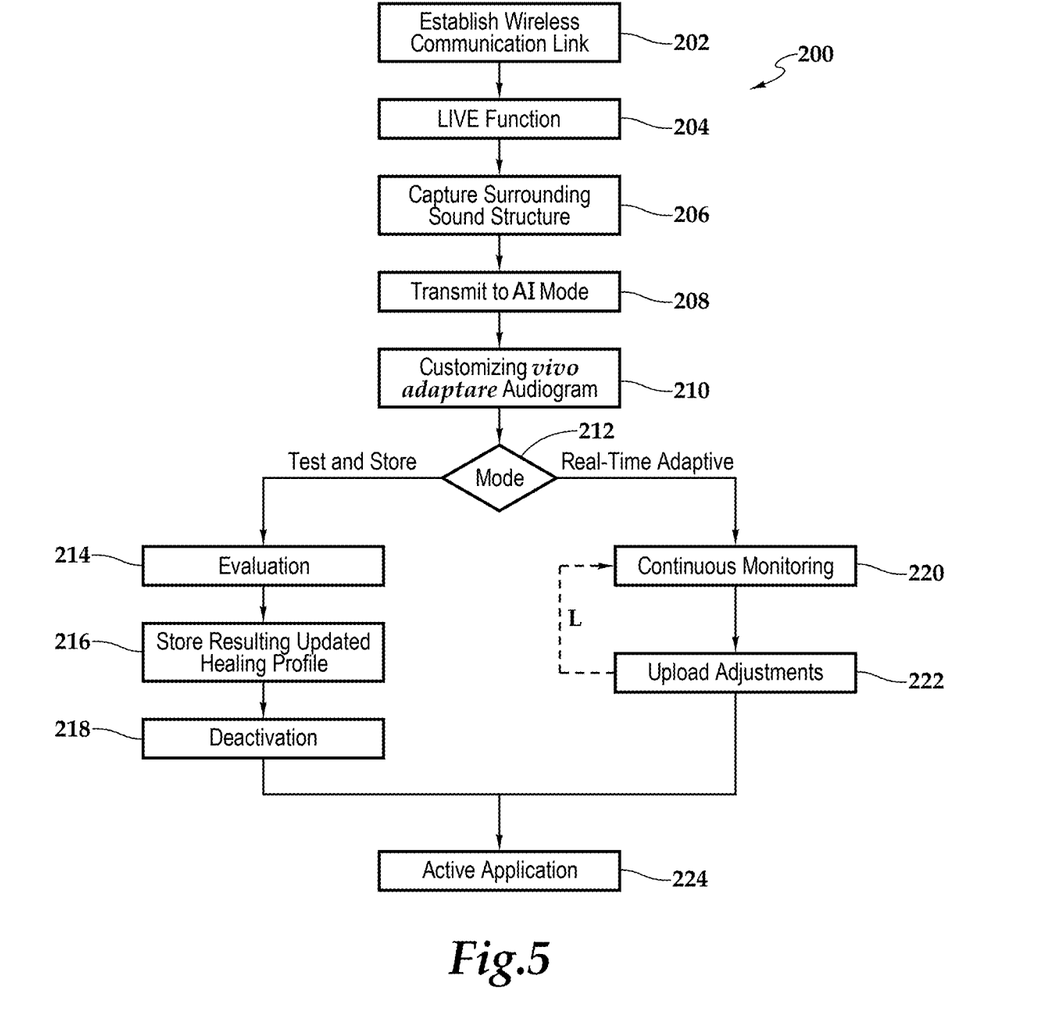
FIG. 5 is a flow chart depicting one embodiment of a method for aiding hearing being utilized according to the teachings presented herein.

Referring now to FIG. 5, a single, consolidated flow chart 200 illustrates one embodiment of a method for operating the hearing aid system. In block 202, a wireless communication link is established between the hearing aid device and a smart device via a transceiver, enabling bidirectional data exchange. In block 204, the user launches a "listening intelligence and frequency enhancement" (LIVE) function on the smart device, which presents available modes—for instance, "Test and Store" or "Real-Time Adaptive." Upon choosing a mode, the system captures ambient sound or the surrounding sound structure using the hearing aid's microphones (block 206) and transmits the data to an artificial intelligence module (block 208). This AI module references a vivo adaptare audiogram of stored hearing profiles, either selecting an existing profile or combining multiple profiles to create a new, customized hearing profile (block 210).

If the user is in "Test and Store" mode at decision block 212, the hearing aid device or AI module evaluates the recorded sound data for a set duration (block 214), stores the resulting updated hearing profile in the vivo adaptare audiogram (block 216), and automatically deactivates the LIVE function (block 218). This mode allows the patient to capture and preserve a newly generated profile—such as a "restaurant noise" setting—for later use, thus accumulating effectively unlimited test criteria.

Conversely, if the user selects "Real-Time Adaptive" mode at decision block 212, the artificial intelligence module continuously monitors changes in the ambient sound data (block 220). It then generates incremental adjustments to one or more frequency segments of the hearing profile and uploads these adjustments to the hearing aid device (block 222) without requiring further user confirmation. The loop L persists as long as real-time adaptation remains active, providing on-the-fly modifications to tackle shifting acoustic environments.

Finally, in block 224, the chosen or newly created profile is actively applied by the hearing aid's electronic signal processor, tailoring audio output to the patient's current listening conditions. Whether "Test and Store" or "Real-Time Adaptive," this integrated methodology empowers users to manage their hearing profiles directly from a smart device, supported by AI-driven analysis and virtually infinite storage of hearing criteria.

The order of execution or performance of the methods and data flows illustrated and described herein is not essential, unless otherwise specified. That is, elements of the methods and data flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A hearing aid system for a patient, the hearing aid system comprising:
a programming interface configured to facilitate bidirectional communication between a hearing aid device and a smart device, the hearing aid device having integrated sound processing capabilities, including a microphone, a speaker, and an electronic signal processor capable of receiving, processing, and outputting audio signals, the smart device including a housing securing a processor, non-transitory memory, a user interface, a transceiver, and storage therein, the smart device including a busing architecture communicatively interconnecting the speaker, the user interface, the processor, the transceiver, the memory, and the storage;

a vivo adaptare audiogram stored within the hearing aid device, the vivo adaptare audiogram comprising a plurality of stored hearing profiles, each profile specifying at least one adjustment to a frequency segment of an overall hearing range, and being selectively combinable with one or more other stored hearing profiles to create a newly generated hearing profile, and the non-transitory memory accessible to the processor, the non-transitory memory including processor-executable instructions that, when executed by the processor, cause the system to:

present, on the user interface, a listening intelligence and frequency enhancement function enabling the patient to initiate an automated analysis of ambient sound captured by the microphone, receive the ambient sound data from the hearing aid device and utilize an artificial intelligence module to compare the ambient sound data with the plurality of stored hearing profiles, automatically select at least one of the stored hearing profiles or generate the newly created hearing profile by combining parameters from multiple stored hearing profiles, activate the selected or newly created hearing profile at the hearing aid device for immediate processing of the ambient sound, and store the activated hearing profile in the vivo adaptare audiogram for future access or modification.

2. The hearing aid system of claim 1, wherein the processor-executable instructions further cause the system to operate in a test and store mode such that, upon activation of the listening intelligence and frequency function, the hearing aid device:

captures ambient sound for a predetermined duration, creates or modifies a hearing profile in response to an outcome of the ambient sound evaluation, and stores the modified or newly created hearing profile in the vivo adaptare audiogram before deactivating the listening intelligence and frequency function.

3. The hearing aid system of claim 1, wherein the processor-executable instructions further cause the system to operate in a real-time adaptive mode such that, upon activation of the listening intelligence and frequency enhancement function, the artificial intelligence module continuously:

monitors changes in the ambient sound data, generates incremental adjustments to at least one frequency segment of the selected or newly created hearing profile, and uploads the incremental adjustments to the hearing aid device without requiring additional user confirmation.

4. The hearing aid system of claim 1, wherein the artificial intelligence module is configured to rank multiple candidate hearing profiles based on at least one of (i) patient usage history, (ii) patient feedback regarding clarity or comfort, and (iii) a measured signal-to-noise ratio in the ambient sound, and to recommend for activation the highest-ranked hearing profile unless overridden by user input.

5. The hearing aid system of claim 1, wherein the plurality of stored hearing profiles includes at least one hearing profile that selectively attenuates background noise in a restaurant environment, at least one hearing profile that enhances speech clarity, and at least one hearing profile designed to minimize wind noise, enabling the listening intelligence and frequency function to automatically combine or switch among these profiles based on detected acoustic conditions.

6. The hearing-aid system of claim 1, wherein the artificial-intelligence module, the signal-processing workload, and the vivo adaptare audiogram are partitionable among the hearing-aid device, the smart device, and at least one remote server.

7. The hearing-aid system of claim 6, wherein latency-critical operations comprising real-time filtering, amplification, and output shaping are performed by the electronic signal processor of the hearing-aid device;

mid-tier analytics and user-interface logic are executed by the processor of the smart device; and computationally intensive tasks, including pattern recognition, profile ranking, or synthesis of composite profiles, are off-loaded to the remote server and synchronized with the smart device when connectivity permits.

8. The hearing-aid system of claim 6, wherein the vivo adaptare audiogram is mirrored or sharded across the hearing-aid device, the smart device, and the remote server so that the most current profile data is accessible to whichever component is selected to execute the next processing step.

9. The hearing-aid system of claim 1, further comprising an autonomous detached-operation mode resident in the hearing-aid device, the mode being enabled by the smart device synchronizing the latest vivo adaptare audiogram and transferring a lightweight inference model to the electronic signal processor before communication with the smart device is interrupted.

10. The hearing-aid system of claim 9, wherein, while operating in the detached-operation mode, the hearing-aid device monitors ambient sound for predefined acoustic triggers associated with stored hearing profiles, autonomously selects or blends the corresponding profiles, and applies resulting frequency-segment adjustments in real time without external guidance.

11. The hearing-aid system of claim 10, wherein the hearing-aid device logs, in non-volatile local memory, profile selections, ambient-sound descriptors, and user-initiated control inputs, and automatically uploads the log to the smart device or the remote server once the communication link is re-established.

12. The hearing-aid system of claim 11, wherein the uploaded log is utilized by the artificial-intelligence module to refine ranking weights, generate improved composite hearing profiles, and provide firmware or audiogram updates to the hearing-aid device.

13. A computer-implemented method of operating a hearing-aid system that includes a hearing-aid device and a smart device, the method comprising:

establishing bidirectional communication between the hearing-aid device and the smart device via a programming interface;

presenting, on a user interface of the smart device, a listening-intelligence and frequency-enhancement (LIVE) function;

capturing ambient sound with at least one microphone of the hearing-aid device and transmitting corresponding sound data to an artificial intelligence (AI) module executed by the smart device;

comparing, by the AI module, the sound data with a plurality of stored hearing profiles maintained in a vivo adaptare audiogram;

automatically selecting at least one stored hearing profile or generating a new hearing profile by combining parameters from multiple stored hearing profiles;

activating the selected or generated hearing profile in the hearing-aid device to process incoming audio signals in real time; and storing the activated hearing profile in the vivo adaptare audiogram for future access or modification.

14. The computer-implemented method of claim 13, further comprising operating in a test-and-store mode in which the hearing-aid device:

captures ambient sound for a predetermined duration, creates or modifies a hearing profile in response to the captured sound, and stores the created or modified profile in the vivo adaptare audiogram before the LIVE function is deactivated.

15. The computer-implemented method of claim 13, further comprising operating in a real-time adaptive mode in which the AI module continuously:

monitors changes in the ambient sound data, generates incremental adjustments to at least one frequency segment of the active hearing profile, and uploads the incremental adjustments to the hearing-aid device without requiring additional user confirmation.

16. The computer-implemented method of claim 13, further comprising:

ranking, by the AI module, multiple candidate hearing profiles based on at least one of (i) patient-usage history, (ii) patient feedback regarding clarity or comfort, and (iii) a measured signal-to-noise ratio; and activating, unless overridden by user input, a highest-ranked hearing profile.

17. A method of detached operation for a hearing-aid device programmed by a smart device, the method comprising:

synchronizing, before detachment, a most-recent vivo adaptare audiogram and a lightweight inference model from the smart device to an electronic signal processor of the hearing-aid device;

subsequently operating the hearing-aid device without the smart device by:

detecting acoustic triggers indicative of predefined listening environments, autonomously selecting or blending at least one stored hearing profile in response to the acoustic triggers, and applying resulting frequency-segment adjustments to incoming audio signals in real time;

logging, in non-volatile memory of the hearing-aid device, each profile selection, a descriptor of the detected acoustic trigger, and any user-initiated control input; and upon re-establishing communication with the smart device or a remote server, uploading the log for further AI processing.

18. The method of claim 17, wherein AI tasks, signal-processing workload, and the vivo adaptare audiogram are dynamically partitioned among the hearing-aid device, the smart device, and at least one remote server such that:

latency-critical operations comprising real-time filtering, amplification, and output shaping are performed by the hearing-aid device, mid-tier analytics and user-interface logic are executed by the smart device, and computationally intensive tasks, including pattern recognition or profile synthesis, are executed by the remote server and synchronized when connectivity permits.

19. The method of claim 17, further comprising mirroring or sharding the vivo adaptare audiogram across the hearing-aid device, the smart device, and the remote server so that most-current profile data is accessible to whichever component next executes a processing step.

20. The method of claim 17, further comprising using the uploaded log to:

refine weighting factors applied by the AI module when ranking candidate hearing profiles, generate improved composite hearing profiles, and push firmware or audiogram updates back to the hearing-aid device.

\* \* \* \* \*